United States Patent [19]

Beck

[11] Patent Number: 4,605,626

[45] Date of Patent: Aug. 12, 1986

[54] ELECTROCHEMICAL SYSTEM WITH ROTATING ELECTRODE/SPARGER ASSEMBLY

[75] Inventor: Theodore R. Beck, Seattle, Wash.

[73] Assignee: Rohrback Technology Corporation, Seattle, Wash.

[21] Appl. No.: 729,209

[22] Filed: May 1, 1985

[51] Int. Cl.[4] .............................................. C12M 1/34
[52] U.S. Cl. .................................. 435/291; 204/403; 204/212; 204/277; 435/313; 435/315; 435/316; 435/817
[58] Field of Search ............... 435/291, 313, 314, 315, 435/316; 204/400, 403, 277, 212, 1 E, 1 T, 280, 199

[56] References Cited

U.S. PATENT DOCUMENTS

| | | | |
|---|---|---|---|
| 646,313 | 3/1900 | Rhodin | 204/212 |
| 1,368,362 | 2/1921 | Sill | 204/277 X |
| 3,506,544 | 4/1970 | Silverman et al. | 204/1 T |
| 4,399,028 | 8/1983 | Kile et al. | 209/164 |
| 4,434,249 | 2/1984 | Ballestrasse et al. | 521/27 |

OTHER PUBLICATIONS

Ser. No. 628,518, Silverman, filed 7/6/84.

*Primary Examiner*—G. L. Kaplan
*Attorney, Agent, or Firm*—Christensen, O'Connor, Johnson & Kindness

[57] ABSTRACT

An electrochemical system for determining the concentration of a bacteria or other enzymatic agents in a liquid sample (14). The system includes mounting means (20) for mounting an electrode assembly (16), and drive means for rotating the electrode assembly. The electrode assembly comprises a shaft (22) having a longitudinal axis and a longitudinally extending interior passage (40), an electrode (24) mounted at the lower end of the shaft, and sparging means (26) extending laterally from the lower end of the shaft. The sparging means is in communication with passage (40) through openings (50). The electrode and sparging means are mounted such that they are immersed in the sample when the shaft is mounted by the mounting means. The electrode assembly further comprises conductor means (44, 46) for electrically connecting the electrode to the electrochemical system. The electrode assembly is rotated during measurement of the concentration of the enzymatic agent. Prior to such measurement, dissolved oxygen may be rapidly removed from the sample by rotating the electrode assembly and introducing an inert gas into the passage, such that the inert gas passes from the rotating sparging means into the sample.

25 Claims, 8 Drawing Figures

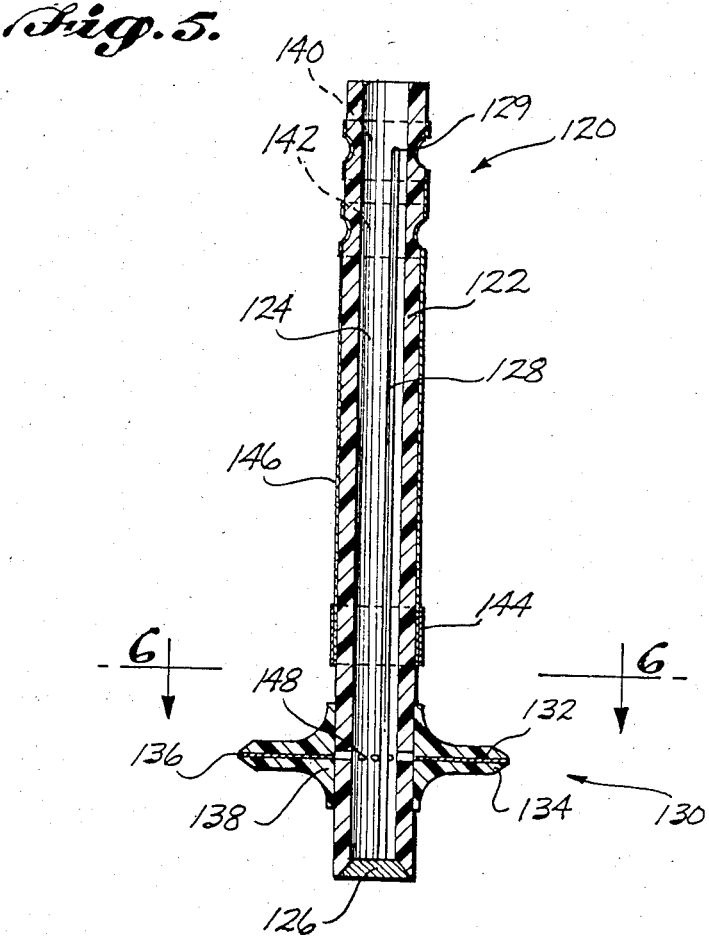
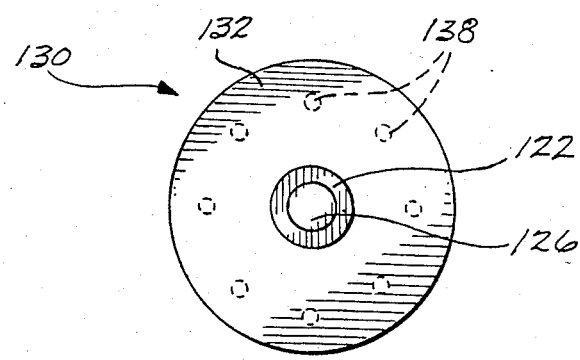

ELECTROCHEMICAL SYSTEM WITH ROTATING ELECTRODE/SPARGER ASSEMBLY

FIELD OF THE INVENTION

The present invention relates to electrochemical systems, and in particular to an electrochemical system that includes gas sparging means.

BACKGROUND OF THE INVENTION

A known and effective technique for determining the microbe or enzyme concentration in a sample involves combining the sample with a substance that undergoes an oxidation-reduction reaction in the presence of the microbe or enzyme, and following the course of the reaction utilizing an electrochemical cell. For example in the presence of glucose, many bacteria metabolize methylene blue as an oxidant to produce the reaction product leuco methylene blue. If the reduction of methylene blue to leuco methylene blue occurs in an electrochemical cell, reoxidation of the leuco methylene blue to methylene blue at the cell anode will give rise to a measurable current that can be related to microbe concentration. This technique is described in greater detail in U.S. Pat. No. 3,506,544.

One of the major advantages of the electrochemical method for determining microbe or enzyme concentration is speed. For example, the traditional plate count method for the detection and enumeration of bacteria typically requires from 24 hours to several days to produce results. The electrochemical method, on the other hand, can typically produce results within an hour or less. Even this great speed increase could be further improved, however, were it not for the need to remove dissolved oxygen from a liquid sample solution prior to the introduction of bacteria and measurement of the resulting current. This need arises because oxidation of leuco methylene blue by dissolved oxygen competes with oxidation at the cell anode, and therefore modifies the measured current. In the past, conventional gas spargers have been used to bubble argon or other inert gases through the sample solution prior to the introduction of the bacteria. Such spargers have typically comprised a Teflon tube having small holes drilled in it, such that gas escaping from the tube forms small bubbles that pass upward through the solution. The time required to decrease the dissolved oxygen to the required level in the electrochemical measurement of leuco methylene blue has been typically 15 minutes to over one hour.

SUMMARY OF THE INVENTION

The present invention provides a rotatable one-piece electrode assembly that includes gas sparging means and that may also include both sensing and reference electrodes. The electrode assembly is capable of making rapid and accurate microbe and enzyme determinations, and is also sufficiently simple in construction to be used on a disposable basis.

In one aspect, the present invention provides an electrode assembly for use in an electrochemical system for determining the concentration of an enzymatic agent in a liquid sample. The electrochemical system includes mounting means for mounting the electrode assembly such that at least the lower end of the electrode assembly is immersed in the sample, and drive means for rotating the electrode assembly. The electrode assembly comprises a shaft having a longitudinal axis and a longitudinally extending interior passage, an electrode fixedly mounted with respect to the shaft, and sparging means mounted to the shaft, the sparging means being in communication with the passage. The electrode and sparging means are mounted such that they are immersed in the sample when the shaft is mounted by the mounting means. The electrode assembly further comprises first conductor means for electrically connecting the electrode to the electrochemical system.

The electrode assembly including the electrode may be rotated during measurement of the concentration of the enzymatic agent. Prior to such measurement, dissolved oxygen may be rapidly removed from the sample by rotating the electrode assembly and introducing an inert gas into the passage, such that the inert gas passes from the rotating sparging means into the sample. In a second aspect, the present invention comprises an electrochemical system that includes the electrode assembly as described above.

The sparging means may comprise means forming at least one conduit extending radially outward from the shaft, such that the inner end of the conduit is in communication with the passage and the outer end of the conduit is open, such that when the sparging means is immersed in the sample, the outer end of the conduit is in communication with the sample. The sparging means may comprise a pair of disk members having central openings through which the shaft extends. The disk members are adhesively secured to their respective central openings to the shaft, and the conduit extends between the disk members from the shaft to the outer edges of the disk members. The sparging means may further comprise gas permeable solid material sandwiched between the disk members. The electrode may be mounted to the lower end of the shaft such that the electrode encloses the lower end of the passage. The electrode assembly may further comprise a second electrode fixedly mounted with respect to the shaft and second conductor means for connecting the second electrode to the electrochemical system. The shaft may be mounted in the mounting means by a detent mechanism that serves the dual purpose of supporting the shaft and establishing an electrical connection between the first conductor means and the electrochemical system.

BRIEF DESCRIPTION OF THE DRAWINGS

FIG. 5 is a cross-sectional view of a second embodiment of the electrode assembly;

FIG. 6 is a cross-sectional view taken along the line 6—6 of FIG. 5;

DETAILED DESCRIPTION OF THE INVENTION

Figure 1:
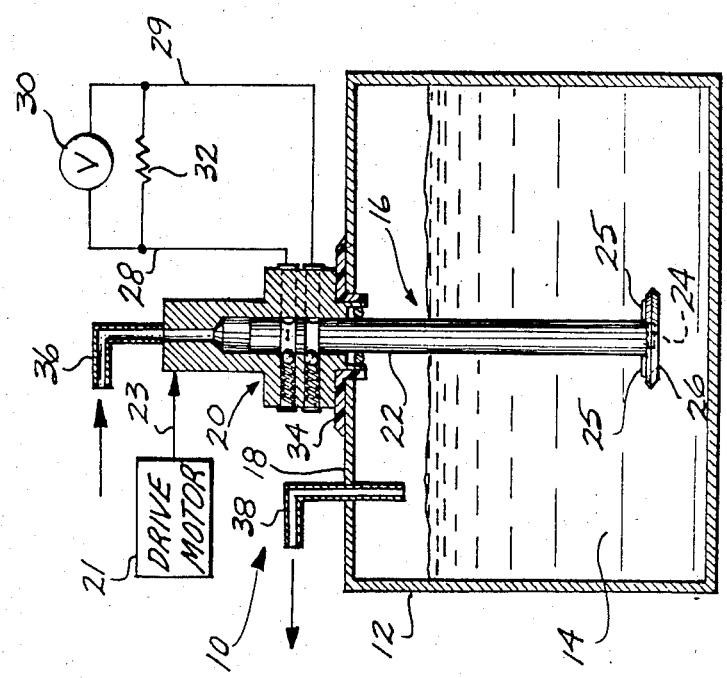
FIG. 1 is a schematic drawing of an electrochemical system according to the present invention.

FIG. 1 schematically illustrates one preferred arrangement of the electrochemical system of the present invention. The illustrated electrochemical system may be used to determine the concentration of an enzymatic agent in a liquid sample. The term "enzymatic agent" includes enzymes and enzyme-containing microbes such as bacteria and yeast. The electrochemical system of FIG. 1 comprises container 12 in which aqueous solution 14 is place through suitable inlet means (not shown). Solution 14 may initially comprise glucose, a buffer, and methylene blue dissolved in the solution. The electrochemical system further comprises electrode assembly 16 that is mounted in upper wall 18 of container 12 by mounting assembly 20, and that extends downward into solution 14. Electrode assembly 16 comprises shaft 22, sensing electrode 24, reference electrode 25 and gas sparger 26. Sensing electrode 24 is positioned at the lower end of shaft 22, gas sparger 26 extends laterally adjacent the lower end of shaft 22, and reference electrode 25 is positioned on the upper surface of the gas sparger. As described below, the sensing and reference electrodes are electrically connected to lines 28 and 29, respectively, such that the electrodes are externally connected to one another through voltmeter 30 and resistor 32. Sensing electrode 24 preferably comprises graphite, and reference electrode 25 preferably comprises a silver/silver chloride electrode.

The upper end of shaft 22 is mounted in mounting assembly 20. The mounting assembly is positioned in upper wall 18 and is in contact with the upper wall through low friction washer 34, such that the mounting assembly is rotatable about its central longitudinal axis. The electrochemical system includes bearing means (not shown) and drive means for supporting the mounting assembly and for rotating the mounting assembly and electrode assembly 16 about the vertical, longitudinal axis of shaft 22. The drive means may comprise electric drive motor 21 connected to the mounting assembly by a conventional drive belt 23. As more fully described below, the interior of shaft 22 includes an interior longitudinal passage in communication with gas sparger 26. Mounting assembly 20 is constructed such that inert gas supplied to the mounting assembly through line 36 flows into the longitudinal passage of shaft 22. From the longitudinal passage, the gas flows into gas sparger 26 for dispersal as bubbles into solution 14. The bubbles pass upward through solution 14, carrying with them dissolved oxygen and other gases, and the inert gas and the oxygen exit from the container via line 38.

To use electrochemical system 10 to determine enzyme or microbe concentration, a buffered solution containing glucose, methylene blue and the microbe or enzyme whose concentration is to be determined is introduced into container 12, and an inert gas such as argon is bubbled into solution 14 through gas sparger 26 while the gas sparger and shaft 22 are rotated by mounting assembly 20. A suitable buffer comprises a mixture of potassium hydrogen phosphate and potassium dihydrogen phosphate, adjusted such that the resulting pH is approximately 7.0. The inert gas proceeds to substantially remove dissolved oxygen from the solution, a process that can be followed by monitoring the current flow through the system. The bubbling of inert gas is continued throughout the subsequent enzyme or microbe determination to maintain solution 14 substantially free of dissolved oxygen. With oxygen removed, the microbe or enzyme in solution 14 proceeds to reduce methylene blue to leuco methylene blue, a process that gives rise to the two following reactions.

Sensing electrode:   $LMB \rightarrow MB + 2e^-$

Reference electrode:   $AgCl + e^- \rightarrow Ag + Cl^-$ where MB and LMB stand for methylene blue and leuco methylene blue respectively. The production of leuco methylene blue by the microbes or enzyme tends to drive the sensing electrode reaction to the right, resulting in an electron current that flows out of the sensing electrode, through line 28 and resistor 32, and then through line 29 and into reference electrode 25. At the reference electrode, the electrons drive the indicated reduction reaction to the right, resulting in the production of chloride ions that pass into solution 14. Current flowing through resistor 32 results in a voltage drop across the resistor that is measured by voltmeter 30. Voltmeter 30 therefore measures the current resulting from the reduction of methylene blue caused by the microbe or enzyme, and the rate of change of such current can be related to microbe or enzyme concentration by calibration in a manner known to those skilled in the art.

Typical rotation speeds for electrode assembly 16 range from 100–2,000 rpm. The rotation of electrode assembly 16 serves two important functions. Rotation of the gas sparger results in the removal of oxygen from solution 14 at a rate significantly higher than that obtained with a nonrotating sparger. Rotation of sensing electrode 24 during measurement of the microbe concentration gives a well defined current related to the concentration of leuco methylene blue as given by the well known Levich equation for diffusion limited current density.

The standard electrode potential of a silver/silver chloride electrode is 0.22 volts with respect to the standard hydrogen electrode. This potential is in the plateau region for oxidation of leuco methylene blue, and it is therefore appropriate to use a silver/silver chloride electrode as a reference electrode. Although other types of electrodes, for example a calomel electrode, can be used as the reference electrode, the use of silver/silver chloride has the advantage that the reference electrode can easily be positioned on gas sparger 26 by applying silver paint to the sparger and then anodizing the silver in chloride solution to produce a silver chloride layer. Resistor 32 must be small enough to ensure that the potential of sensing electrode 24 is not significantly less than the potential of reference electrode 25. In a typical electrochemical system, the current flowing through resistor 32 is typically on the order of microamperes or less, and a suitable value for resistor 32 is therefore 1 kilohm.

The particular electrochemical system illustrated in FIG. 1 has been selected for purposes of illustration only. It is to be understood, however, that the present invention can be applied to electrochemical systems that are not based upon the reduction of methylene blue, and to electrochemical systems that employ different techniques for measuring electrode current or potential.

Figure 2:
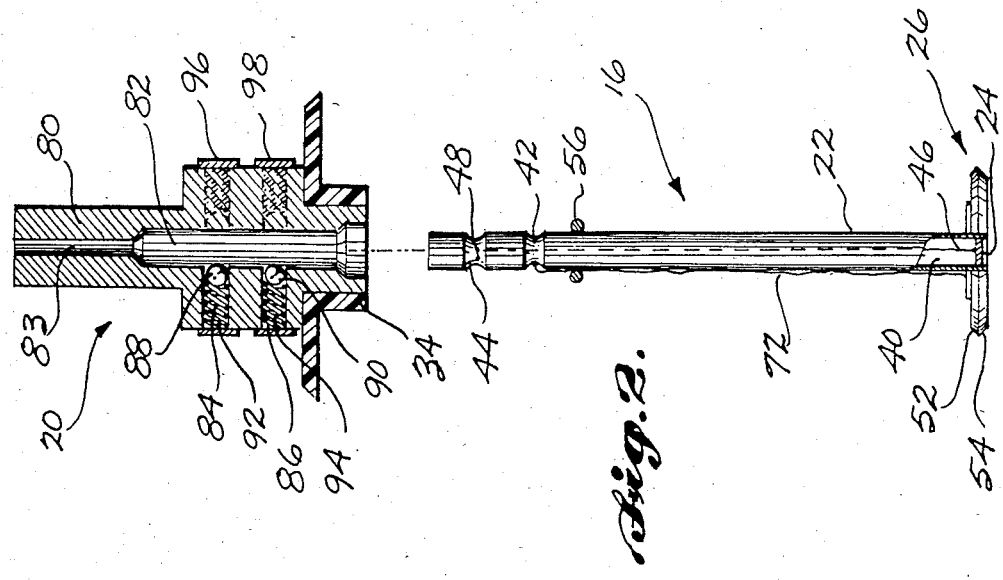
FIG. 2 is a combined side elevational and cross-sectional view of the electrode assembly and mounting assembly.
Figure 3:
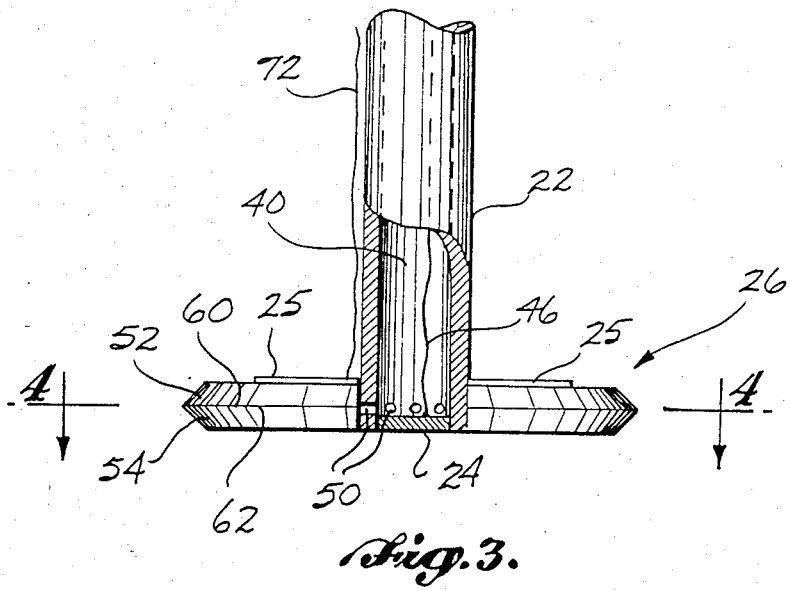
FIG. 3 is a partially cut away side elevational view of the lower end of the electrode assembly.
Figure 4:
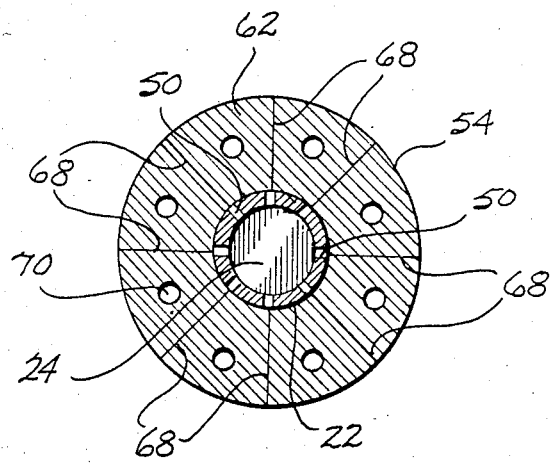
FIG. 4 is a cross-sectional view taken along the line 4—4 of FIG. 3.

Electrode assembly 16 and mounting assembly 20 are illustrated in greater detail in FIGS. 2–4. Electrode assembly 16 comprises shaft 22 that includes central longitudinal passage 40 and electrical contacts 42 and 44 near the top of the shaft. Each contact 42 and 44 occupies a concave recess encircling shaft 22, and comprises a conductive material such as silver paint. Sensing electrode 24 is adhesively mounted to the lower end of shaft 22, such that the sensing electrode enclosed the lower end of passage 40. Electrical connection to sensing electrode 24 is established by means of bus 46 positioned in passage 40 of shaft 22. Bus 46 may be any suitable conductor, such as a copper wire or a stripe of silver or graphite paint. Near the upper end of shaft 22, bus 46 passes through opening 48 in the shaft, and thereby establishes electrical connection with contact 44 on the outer surface of the shaft.

The lower end of shaft 22 includes openings 50 through which gas can escape out of passage 40. Gas sparger 26 is positioned around openings 50, the gas sparger including Plexiglas washers 52 and 54 that are adhesively secured to one another along facing surfaces 60 and 62 respectively, and that are adhesively secured to shaft 22 along portions of their inner diameters. Referring to FIG. 4, surface 62 comprises a plurality of grooves 68 that extend radially from the inner to outer circumference of washer 54. The grooves are aligned with openings 50, such that gas exiting from shaft 22 through openings 50 can pass through the grooves into solution 14. Numeral 70 in FIG. 4 identifies one of the adhesive spots that are used to secure washers 52 and 54 to one another along surfaces 60 and 62 respectively. Reference electrode 25 comprises a silver/silver chloride electrode that is located on the upper surface of washer 52. The reference electrode is electrically connected to contact 42 by silver paint bus 72, bus 72 being applied directly to the outer surface of shaft 22. The silver/silver chloride electrode and bus are coated with an anion conducting ion exchange resin to prevent dissolution of silver ion in chloride solutions such as solution 14, which dissolution could be toxic to the bacteria and lead to an erroneous determination of bacteria concentration. A coating of a resin composed of copolymerized methyl methacrylate and methacrylamidopropyltrimethylammonium chloride as described in U.S. Pat. No. 4,434,249 has been found effective.

Referring now specifically to FIG. 2, mounting assembly 20 comprises housing 80 that includes connected vertical central passages 82 and 83, and lateral passages 84 and 86 that extend from central passage 82 to the outer circumference of the housing. Metal balls 88 and 90 and metal springs 92 and 94 are mounted within lateral openings 84 and 86, respectively. Each spring biases its corresponding ball inwardly against a stop (not shown) at the inward end of its respective lateral passage, such that the balls normally extend a short distance into central passage 82. Metal bands 96 and 98 encircle housing 80 over lateral passages 84 and 86, respectively, such that the bands contact and compress springs 92 and 94, respectively. Bands 96 and 98 are thereby in electrical contact with balls 88 and 90 respectively. Conventional brushes (not shown) may be employed to electrically connect bands 96 and 98 to lines 28 and 29.

Electrode assembly 16 is mounted in mounting assembly 20 by inserting the upper end of shaft 22 into passage 82 such that balls 88 and 90 are received in the recesses underlying contacts 44 and 42, respectively. The balls and recesses thereby form a detent mechanism that secures the shaft in the mounting assembly. The balls in addition establish electrical contact between rings 96 and 98 and contacts 44 and 42, respectively, thereby establishing electrical connection between the sensing and reference electrodes and lines 28 and 29, respectively (FIG. 1). "O" ring 56 seals the connection between shaft 22 and mounting assembly 20, and functions to prevent solution 14 from splashing into the electrical contacts 42-90 and 44-88 and to prevent inert gas from escaping without going through gas sparger 26.

A second preferred embodiment of the electrode assembly is illustrated by electrode assembly 120 of FIGS. 5 and 6. Electrode assembly 120 comprises shaft 122 that includes central longitudinal passage 124. Sensing electrode 126 is adhesively secured to the lower end of shaft 122 such that the sensing electrode encloses the lower end of passage 124. The sensing electrode preferably comprises graphite. Electrical contacts 140 and 142 encircle shaft 122 near the upper end thereof. Contacts 140 and 142 are essentially identical to contacts 44 and 42 respectively of the embodiment of FIGS. 1-4. Sensing electrode 126 is electrically connected to contact 140 by silver bus 128 that extends longitudinally through passage 124 and laterally through opening 129 in shaft 122. Gas sparger 130 is positioned around shaft 122 a short distance from the lower end of the shaft. Gas sparger 130 has a sandwich structure comprising stamped plastic rings 132 and 134 adhesively secured to shaft 122, and disk 136 positioned between the rings. Disk 136 comprises a gas permeable solid material such as cloth or other woven material or paper. Rings 132 and 134 are secured to one another and to disk 136 by adhesive spots 138, each adhesive spot extending through pores in disk 136. The inner circumference of disk 136 is in communication with passage 124 through openings 148 in the shaft.

Reference electrode 144 comprises a silver/silver chloride electrode disposed circumferentially about shaft 122 above gas sparger 130. The reference electrode is electrically connected to contact 142 by silver bus 146 that extends up the outside of shaft 122. The electrode assembly of FIG. 5 is adapted to be used with a suitable mounting assembly, such as mounting assembly 20 of FIGS. 1-2.

Figure 7:
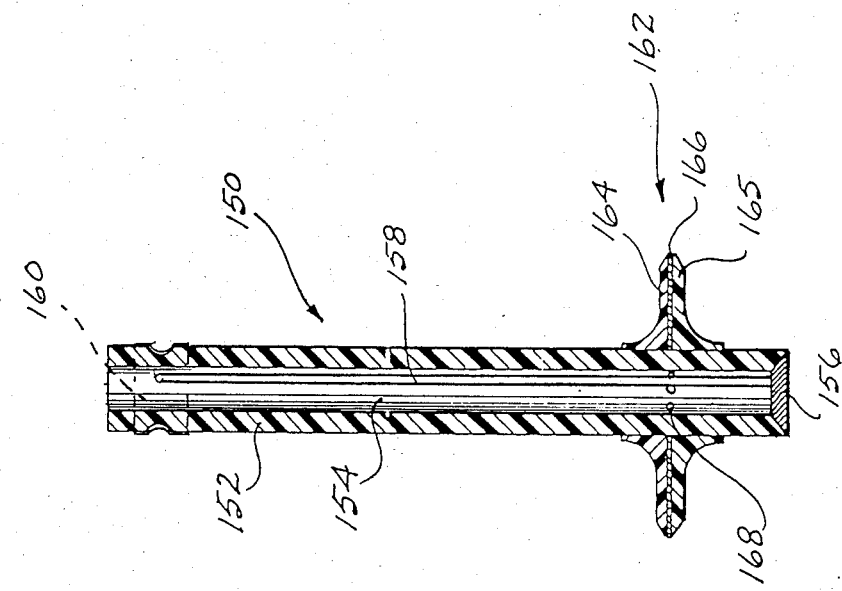
FIG. 7 is a cross-sectional view of a third embodiment of the electrode assembly.

A third preferred embodiment of the electrode assembly is illustrated by electrode assembly 150 of FIG. 7. Electrode assembly 150 comprises shaft 152 having central longitudinal passage 154 formed therein. Sensing electrode 156 is secured to the lower end of shaft 152, such that the reference electrode encloses the lower end of passage 154. Silver bus 158 is positioned in passage 154 and connects the sensing electrode to contact 160 that extends circumferentially about shaft 152 near the upper end of the shaft. Gas sparger 162 is similar to gas sparger 130 of the embodiment of FIG. 5, and comprises rings 164 and 165 that are adhesively secured to shaft 152 and that mount paper or cloth disk 166 between the rings. Communication between passage 154 and gas sparger 162 is provided by openings 168 in shaft 152.

The electrode assembly 150 of FIG. 7 is adapted for use in an electrochemical system wherein a second electrode (the reference electrode) separate from the electrode assembly extends into the sample solution. The reference electrode may comprise a simple wire or cylindrical rod extending downward into the solution from upper wall 18 (FIG. 1). The mounting assembly for electrode assembly 150 may be similar to mounting assembly 20, with ball 88 and associated elements eliminated if desired.

Figure 8:
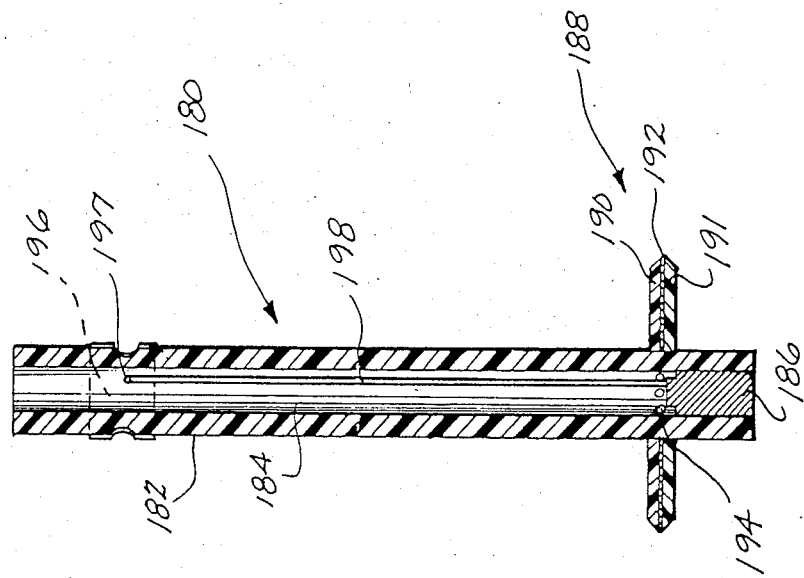
FIG. 8 is a cross-sectional view of a fourth embodiment of the electrode assembly.

A fourth embodiment of the electrode assembly is illustrated by electrode assembly 180 of FIG. 8. Electrode assembly 180 comprises shaft 182 having central longitudinal passage 184 formed therein. Sensing electrode 186 is mounted to the lower end of shaft 182 and encloses the lower end of passage 184. The sensing electrode comprises a graphite column having an appreciable height, the lower end of the sensing electrode being flush with the lower end of shaft 182. The sensing electrode is electrically connected to contact 196 by silver bus 198, the silver bus extending through opening 197 in shaft 182. Gas sparger 188 is mounted to shaft 182 a short distance above the sensing electrode. Sparger 188 comprises Plexiglas washers 190 and 191 that are adhesively secured to shaft 182, and cloth or paper disk 192 held between the Plexiglas washers. Openings 194 in shaft 182 provide communication between passage 184 and the gas sparger. The electrode assembly of FIG. 8 is designed to be a reusable electrode assembly. After each microbe or enzyme determination, the lower end of the electrode assembly, including the exposed face of sensing electrode 186, is ground away to expose a clean and polished sensing electrode surface for use in a subsequent determination.

While the preferred embodiments of the invention have been illustrated and described, it should be understood that variations will be apparent to those skilled in the art. Accordingly, the invention is not to be limited to the specific embodiments illustrated and described, and the true scope and spirit of the invention are to be determined by reference to the following claims.

The embodiments of the invention in which an exclusive property or privilege is claimed are defined as follows:

1. An electrode assembly for use in an electrochemical system for determining the concentration of an enzymatic agent in a liquid sample, the electrochemical system including mounting means for mounting the electrode assembly such that at least the lower end of the electrode assembly is immersed in the sample and drive means for rotating the electrode assembly, the electrode assembly comprising:
   a shaft having a longitudinal axis and a longitudinally extending interior passage;
   an electrode mounted in a fixed position with respect to the shaft such that when the shaft is mounted by the mounting means, the electrode is immersed in the sample;
   sparging means mounted to the shaft such that the sparging means is immersed in the sample when the shaft is mounted by the mounting means, the sparging means being in communication with the passage; and
   first conductor means for electrically connecting the electrode to the electrochemical system;
   whereby rotation of the electrode assembly by the drive means and introduction of an inert gas into the passage results in the rapid removal of dissolved oxygen from the sample.

2. The electrode assembly of claim 1, wherein the sparging means comprises means forming at least one conduit extending radially outward from the shaft, the inner end of the conduit being in communication with the passage and the outer end of the conduit being open such that when the sparging means is immersed in the sample, the outer end of the conduit is in communication with the sample.

3. The electrode assembly of claim 2, wherein the electrode is mounted to the lower end of the shaft such that the electrode enclosed the lower end of the passage.

4. The electrode assembly of claim 2, wherein the sparging means comprises a pair of disk members having central openings through which the shaft extends, the disk members being adhesively secured at their respective central openings to the shaft, the conduit extending between the disk members from the shaft to the outer edges of the disk members.

5. The electrode assembly of claim 4, wherein each disk member includes an essentially planar surface, the disk members being adhesively joined to each other at their respective planar surfaces, at least one disk member including at least one radial groove extending from the central opening of the disk member to the outer edge of the disk member, each radial groove forming one of the conduits when the disk members are joined to one another.

6. The electrode assembly of claim 4, wherein the sparging means comprises gas permeable solid material sandwiched between the disk members.

7. The electrode assembly of claim 1, further comprising a second electrode fixedly mounted with respect to the shaft and second conductor means for electrically connecting the second electrode to the electrochemical system.

8. The electrode assembly of claim 7, wherein the second electrode comprises a silver/silver chloride electrode coated with an anion conducting ion exchange resin.

9. The electrode assembly of claim 8, wherein the second electrode comprises anodized silver paint positioned on the sparger means.

10. The electrode assembly of claim 7, wherein the first conductor means comprises a first conductor positioned in the passage and the second conductor means comprises a second conductor externally mounted to the shaft.

11. The electrode assembly of claim 10, wherein the first conductor means comprises a first conductive ring encircling the shaft, the first conductor extending through a lateral opening in the shaft to make contact with the conductive ring.

12. The electrode assembly of claim 11, wherein the second conductor means comprises a second conductive ring encircling the shaft adjacent to but not in contact with the first conductive ring.

13. An electrochemical system for determining the concentration of an enzymatic agent in a liquid sample, comprising:
   a container for enclosing the sample;
   a shaft having a longitudinal axis and a longitudinally extending interior 5 passage;
   an electrode mounted in a fixed position with respect to the shaft;
   sparging means mounted to the shaft, the sparging means being in communication with the passage;
   mounting means for mounting the shaft such that the electrode and the sparging means are immersed in the sample;
   first conductor means for electrically connecting the electrode to the mounting means when the shaft is mounted by the mounting means; and drive means for rotating the shaft about the longitudinal axis;

whereby rotation of the shaft by the drive means and introduction of an inert gas into the passage results in the rapid removal of dissolved oxygen from the sample.

14. The electrochemical system of claim 13, wherein the sparging means comprises means forming at least one conduit extending radially outward from the shaft, the inner end of the conduit being in communication with the passage and the outer end of the conduit being open such that when the sparging means is immersed in the sample, the outer end of the conduit is in communication with the sample.

15. The electrochemical system of claim 14, wherein the electrode is mounted to the lower end of the shaft such that the electrode encloses the lower end of the passage.

16. The electrochemical system of claim 14, wherein the sparging means comprises a pair of disk members having central openings through which the shaft extends, the disk members being adhesively secured at their respective central openings to the shaft, the conduit extending between the disk members from the shaft to the outer edges of the disk members.

17. The electrochemical system of claim 16, wherein each disk member includes an essentially planar surface, the disk members being adhesively joined to each other at their respective planar surfaces, at least one disk member including at least one radial groove extending from the central opening of the disk member to the outer edge of the disk member, each radial groove forming one of the conduits when the disk members are joined to one another.

18. The electrochemical system of claim 16, wherein the sparging means comprises gas permeable solid material sandwiched between the disk members.

19. The electrochemical system of claim 13, further comprising a second electrode fixedly mounted with respect to the shaft and second conductor means for electrically connecting the second electrode to the measurement means when the shaft is mounted by the mounting means.

20. The electrochemical system of claim 19, wherein the second electrode comprises a silver/silver chloride electrode coated with an anion conducting ion exchange resin.

21. The electrochemical system of claim 20, wherein the second electrode comprises anodized silver paint positioned on the sparger means.

22. The electrochemical system of claim 19, wherein the first conductor means comprises a first conductor positioned in the passage and the second conductor means comprises a second conductor externally mounted to the shaft.

23. The electrochemical system of claim 22, wherein the first conductor means comprises a first conductive ring encircling the shaft, the first conductor extending through a lateral opening in the shaft to make contact with the conductive ring.

24. The electrochemical system of claim 23, wherein the second conductor means comprises a second conductive ring encircling the shaft adjacent to but not in contact with the first conductive ring.

25. The electrochemical system of claim 13, wherein the first conductor means comprises a conductive ring encircling the shaft and a first conductor positioned in the passage and extending through a lateral opening in the shaft to make contact with the conductive ring, wherein the shaft and mounting means include a detent mechanism for holding the shaft in the mounting means, the detent mechanism including a recess underlying the conductive ring and a conductive element resiliently mounted in the mounting means such that the conductive element mates with the recess when the shaft is mounted in the mounting, thereby securing the shaft in the mounting means and making electrical contact between the mounting means and the conductive ring.

* * * * *

UNITED STATES PATENT AND TRADEMARK OFFICE
CERTIFICATE OF CORRECTION

PATENT NO. : 4,605,626

DATED : August 12, 1986

INVENTOR(S) : Theodore R. Beck

It is certified that error appears in the above-identified patent and that said Letters Patent is hereby corrected as shown below:

Column 3, line 12, "place" should be --placed--

Column 5, line 7, "enclosed" should be --encloses--

Column 8, line 5, "enclosed" should be --encloses-- line 58, delete "5" after "interior"

Signed and Sealed this

Eleventh Day of November, 1986

Attest:

DONALD J. QUIGG

*Attesting Officer*  *Commissioner of Patents and Trademarks*